United States Patent
Lantzsch et al.

(12) 
(10) Patent No.: US 6,603,025 B1
(45) Date of Patent: Aug. 5, 2003

(54) METHOD OF PRODUCTION OF BENZOFURANONE OXIMES

(75) Inventors: Reinhard Lantzsch, Wuppertal (DE); Herbert Gayer, Monheim (DE); Peter Gerdes, Aachen (DE); Walter Hübsch, Wuppertal (DE); Lubbertus Mulder, Hagen (DE); Bernd Gallenkamp, Wuppertal (DE); Matthias Decker, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/130,040

(22) PCT Filed: Nov. 3, 2000

(86) PCT No.: PCT/EP00/10826
§ 371 (c)(1),
(2), (4) Date: May 13, 2002

(87) PCT Pub. No.: WO01/36405
PCT Pub. Date: May 25, 2001

(30) Foreign Application Priority Data

Nov. 16, 1999 (DE) .......................................... 199 54 936

(51) Int. Cl.[7] .............................................. C07D 307/78
(52) U.S. Cl. ..................................... 549/467; 549/466
(58) Field of Search ................................. 549/467, 466

(56) References Cited

FOREIGN PATENT DOCUMENTS

EP          846 691         6/1998

OTHER PUBLICATIONS

Chem. Ber., 33, (month unavailable) 1900, pp. 1398–1407, C.A. Bischoff: Studien über Verkettungen. XLIX. Derivate der drei Oxybenzoësäureähylester.

Chem. Ber., 46 (month unavailable) 1913, pp. 3366–3379, Richard Meyer und Casimir Duczmal, Umsetzungen von Chlor–essigsäure mit Phenol–carbonsäuren und Nitro–phenolen.

Chemistry of Heterocyclic Compounds, 29, (date unavailable) pp. 210–296, Benzofuranones.

J. Chem. Soc. (month unavailable) 1932, pp. 1380–1388, Alexander Robertson, "Experiments on the Synthesis of Rotenone and its Derivatives. Part II. The Synthesis of Rissic Acid and of Derric Acid, and the Constitution of Rotenone, Degeulin, and Tephrosin".

*F. W. Lictenthaler et al.: "Selective Deacetylation . . . ", Tetrahedron, Bd. 21, 1980, Seiten 1425–1428, XP002163748, Elsevier Science Publishers, Amsterdam. NL ISSN: 0040–4020 das ganze Dokument.

*A.R. Katritzky, A.J. Boulton: "Advances in Heterocyclic Chemistry, Vo. 18", 1975 Academic Press, New York, XP002163750 in der Anmeldung erwähnt Verbindungen 282 und 283 Seite 434 –Seite 435.

*C.F. Carvalho et al.: "Naturally occuring dibenzofurans . . . " Journal of The Chemical Society, Perkin Transactions 1., 1984, Seiten 1605–1612, XP002163749, Chemical Society. Letchworth., GB ISSN: 1472–7781 in der Anmeldung erwähmnt Seite 1606 Verbindung 28 Seite 1609.

*Primary Examiner*—Amelia Owens
(74) *Attorney, Agent, or Firm*—Richard E. L. Henderson; Raymond J. Harmuth

(57) ABSTRACT

The present invention relates to a novel process for preparing known benzofuranone oximes, and to a novel process for preparing known benzofuranyl alkanoates which are used as intermediates in the synthesis sequence.

8 Claims, No Drawings

METHOD OF PRODUCTION OF BENZOFURANONE OXIMES

The present invention relates to a novel process for preparing known benzofuranone oximes, and to a novel process for preparing known benzofuranyl alkanoates which are used as intermediates in the synthesis sequence.

It is already known that benzofuranone oximes of the formula (D) can be obtained by the following synthesis sequence:

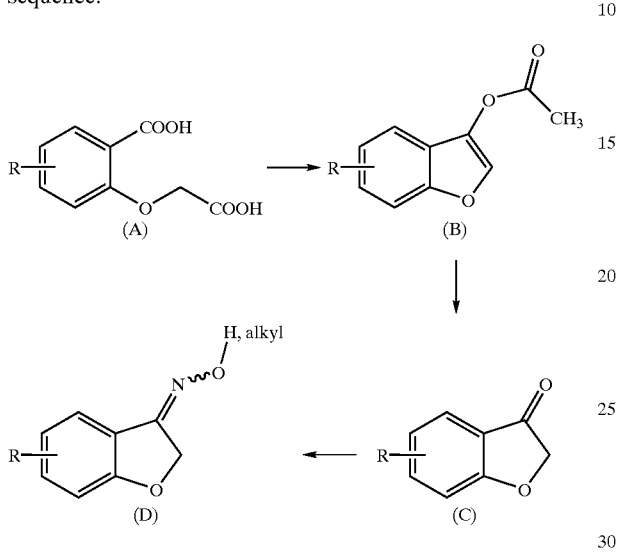

In the first step of the synthesis, a salicylic acid derivative of the formula (A) (compare, for example, J. Chem. Soc. 1932, 1380; Chem. Ber. 33, 1398, (1900); Chem. Ber. 46, 3370, (1913)) is heated with acetic anhydride and sodium acetate, if appropriate in the presence of glacial acetic acid (compare, for example, Adv. Het. Chem. 18, 434 and J. Chem. Soc. Perkin Trans, I, 1984, 1605–1612). The disadvantages of the described processes are firstly the unsatisfactory yields of the corresponding benzofuranyl acetate of the formula (B) and, in particular, the by-product of the formula (E) which is formed in the reaction:

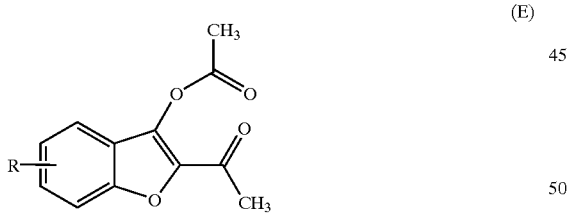

This by-product, which is formed in amounts of up to 10%, is very difficult to separate from the desired product and is thus very particularly disadvantageous for the known processes for preparing benzofuranyl acetates of the formula (B).

In the next step, the benzofuranyl acetates of the formula (B) are hydrolyzed to the benzofuranones of the formula (C) (compare, for example, J. Chem. Soc. Perkin Trans, I, 1984, 1609). This step likewise gives only unsatisfactory yields. Furthermore, the benzofuranones of the formula (C) are chemically unstable and cannot be stored (compare, for example, The Chemistry of Heterocyclic Compounds, 29, 226).

The synthesis of the benzofuranone oximes of the formula (D) from the benzofuranones of the formula (C) and appropriate hydroxylamine derivatives has likewise been described (compare, for example, Chem. Ber. 33, 3178 (1900) and EP-A 846691). This process step has the disadvantage that the unstable benzofuranones are used as starting materials.

It has now been found that a) Benzofuranone oximes of the formula (I),

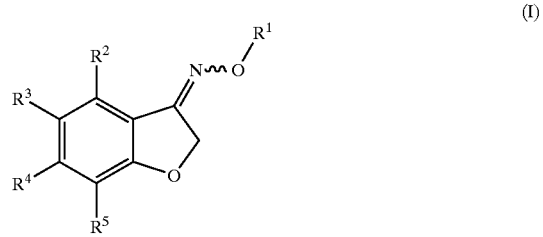

in which
$R^1$ represents hydrogen or alkyl and
$R^2$, $R^3$, $R^4$ and $R^5$ are identical or different and independently of one another each represents hydrogen, alkyl, alkoxy, halogenoalkyl or halogen
are obtained when benzofuranyl alkanoates of the general formula (II),

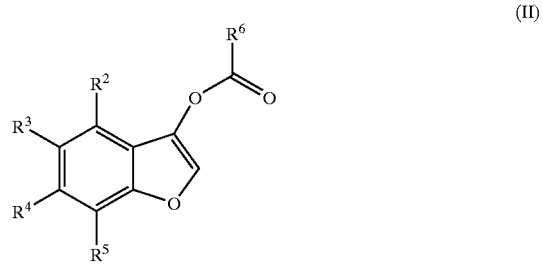

in which
$R^2$, $R^3$, $R^4$ and $R^5$ are each as defined above and
$R^6$ represents alkyl, are hydrolyzed using an acid, if appropriate in the presence of a diluent, and the resulting benzofuranone of the formula (III),

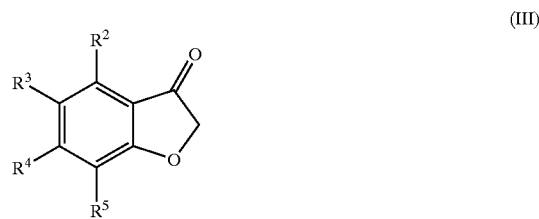

in which
$R^2$, $R^3$, $R^4$ and $R^5$ are each as defined above, is reacted without work-up with a hydroxylamine derivative of the formula (IV),

in which
$R^1$ is as defined above,
or an acid addition complex thereof, if appropriate in the presence of a diluent and if appropriate in the presence of a buffer medium.

The formula (II) provides a general definition of the benzofuranyl alkanoates required as starting materials for carrying out the process according to the invention. Preference is given to using compounds of the formula (II), in which R$^2$, R$^3$, R$^4$ and R$^5$ are identical or different and independently of one another each represents hydrogen, alkyl or alkoxy having in each case 1 to 4 carbon atoms, halogenomethyl or halogen and R$^6$ represents alkyl.

Particular preference is given to preparing benzofuranyl alkanoates of the formula (II), in which R$^2$, R$^3$, R$^4$ and R$^5$ are identical or different and independently of one another each represents hydrogen, methyl, methoxy, t-butyl, trifluoromethyl, fluorine, chlorine or bromine, where very particularly preferably at least three of the substituents R$^2$ to R$^5$ represent hydrogen, and R$^6$ represents methyl, ethyl, n- or i-propyl, n-, i-, s- or t-butyl.

R$^6$ generally particularly preferably represents methyl or ethyl.

The benzofuranyl alkanoates of the formula (II) are known and can be prepared by known methods (compare, for example, Adv. Het. Chem. 18, 434 and J. Chem. Soc. Perkin Trans, I, 1984, 1605–1612).

It is extremely surprising that the benzofuranone formed as intermediate in the reaction mixture does not suffer partial decomposition in the form of oxidation or polymerization, as described in the literature, but reacts immediately with the hydroxylamine derivative of the formula (IV) to give the desired end product in very high purity.

The process a) according to the invention has a number of advantages. Thus, benzofuranoneamines can be prepared in high yields and purities from easily obtainable starting materials under technically simple conditions.

The formula (IV) provides a general definition of the hydroxylamine derivatives and their acid addition complexes furthermore required as starting materials for carrying out the process a) according to the invention. In this formula (IV), R$^1$ represents hydrogen or methyl. Preferred acid addition complexes of compounds of the formula (IV) are the hydrochlorides or hydrogen sulphates or sulphates.

The preferred compound of the formula (IV) is O-methylhydroxylamine. Particular preference is given to hydroxylamine or its acid addition complexes.

The hydroxylamine derivatives of the formula (IV) and their acid addition complexes are known chemicals for synthesis.

It has furthermore been found that b) benzofuranyl alkanoates of the general formula (II) are obtained when salicylic acid derivatives of the formula (V),

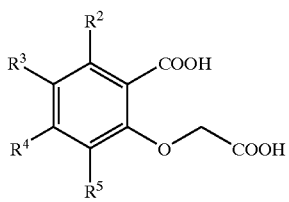

(V)

in which

R$^2$, R$^3$, R$^4$, R$^5$ are each as defined above are reacted with aliphatic acid anhydrides of the formula (VI)

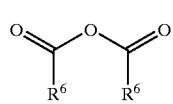

(VI)

in which

R$^6$ is as defined above or aliphatic acyl chlorides of the formula (VII),

(VII)

in which

R$^6$ is as defined above in the presence of a catalyst.

It is extremely surprising that the formation of the by-product described in the literature, which is troublesome and difficult to remove, is suppressed virtually completely.

The process b) according to the invention has a number of advantages. Thus, benzofuranyl alkanoates can be obtained in high yields and purities from easily obtainable starting materials under technically very simple conditions.

The formula (V) provides a general definition of the salicylic acid derivatives required as starting materials for carrying out the process b) according to the invention. In this formula (V), R$^2$, R$^3$, R$^4$ and R$^5$ each preferably or in particular have those meanings which have already been mentioned in connection with the description of the compounds of the formula (II) as being preferred or as being particularly preferred for R$^2$, R$^3$, R$^4$ and R$^5$.

The salicylic acid derivatives of the general formula (V) are known and can be prepared by known methods (compare, for example, J.Chem. Soc. 1932, 1380; Chem. Ber. 33, 1398, (1900); Chem. Ber. 46, 3370, (1913)).

The formula (VI) provides a general definition of the carboxylic anhydrides furthermore required as starting materials for carrying out the process b) according to the invention. In this formula (VI), R$^6$ preferably or in particular has that meaning which has already been mentioned in connection with the description of the compounds of the formula (IV) as being preferred or as being particularly preferred for R$^6$.

The formula (VII) provides a general definition of the carbonyl chlorides furthermore alternatively required as starting materials for carrying out the process b) according to the invention. In this formula (VII), R$^6$ preferably or in particular has that meaning which has already been mentioned in connection with the description of the compounds of the formula (II) as being preferred or as being particularly preferred for R$^6$.

The carboxylic anhydrides of the formula (VI) and the carbonyl chlorides of the formula (VII) are known chemicals for synthesis.

Suitable diluents for carrying out the first and the second step of the process a) according to the invention are inert organic solvents. By way of example and by way of preference, these include ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; or alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

Suitable diluents for carrying out the first and the second step of the process a) according to the invention are preferably alcohols, in particular ethanol, particularly preferably methanol.

The first step of the process a) according to the invention is carried out in the presence of an acid. Suitable acids are all inorganic and organic protic acids, and also all polymeric acids. By way of example and by way of preference, these include hydrogen chloride, sulphuric acid, phosphoric acid, formic acid, acetic acid, trifluoroacetic acid, methanesulphonic acid, trifluoromethanesulphonic acid, toluenesulphonic acid, acidic ion exchangers, acidic alumina and acidic silica gel. Preferred acids are hydrochloric acid and sulphuric acid.

If appropriate, the second step of the process a) according to the invention is carried out in the presence of a buffer medium. Preference is given to a pH from 3 to 7. Suitable buffer media are all customary acid/salt mixtures which buffer the pH in this range. Preference is given to the mixture acetic acid/sodium acetate. In a particular embodiment, after the first intermediate of the process a) according to the invention has reacted, such an amount of sodium acetate and/or aqueous sodium hydroxide solution is added to the reaction mixture that the mixture reaches the desired pH.

When carrying out the first step of the process a) according to the invention, the reaction temperatures can be varied within a relatively wide range. In general, the first step is carried out at temperatures from 20° C. to 120° C., preferably at temperatures from 40° C. to 100° C.

The second step of the process a) according to the invention is generally carried out at temperatures from 0° C. to 80° C., preferably at temperatures from 20° C. to 60° C.

The first and the second step of the process a) according to the invention are generally carried out under atmospheric pressure. However, it is also possible to operate under elevated pressure—in general up to 10 bar.

For carrying out the process a) according to the invention for preparing the compounds of the formula (I), in general from 1 to 5 mol, preferably from 1 to 2 mol, of hydroxylamine derivative of the formula (IV) are employed per mole of the benzofuranyl alkanoate of the formula (II).

The process a) according to the invention is generally carried out as follows: the benzofuranyl alkanoate of the formula (II) is, preferably in the presence of a diluent, admixed with an acid and then heated. After the hydrolysis has ended, the mixture is cooled, preferably to a temperature of from 35 to 45° C., admixed with the hydroxylamine derivative of the formula (IV), or its acid addition complex, and the buffer medium and heated once more. If appropriate, the pH is adjusted accurately by addition of a base, for example aqueous sodium hydroxide. After the reaction has ended, the mixture is worked up in a customary manner. For example, volatile solvent components are distilled off and the mixture is admixed with water, resulting in the crystallization of the product.

If the process b) is carried out using an acid anhydride of the formula (VI), the diluents used are inert organic solvents, or, preferably, the process is carried out in the absence of a solvent.

If the process b) is carried out using an acyl chloride of the formula (VII), the solvents used are inert organic solvents. Preference is given to using aromatic hydrocarbons, such as toluene or chlorobenzene.

The process b) according to the invention is preferably carried out in the presence of a suitable catalyst. Suitable catalysts are all customary organic bases. These preferably include tertiary amines, such as trimethylamine, triethylamine, tributylamine, N,N-dimethylaniline, N,N-dimethyl-benzylamine, pyridine, picolines, 2-methyl-5-ethyl-pyridine, N-methylpiperidine, N-methylmorpholine, N,N-dimethylaminopyridine, diazabicyclooctane (DABCO), diazabicyclononene (DBN) or diazabicycloundecene (DBU). Preference is given to pyridine, N,N-dimethylaminopyridine, picolines and 2-methyl-5-ethyl-pyridine. Particular preference is given to pyridine derivatives, in particular pyridine.

When carrying out the process b) according to the invention, the reaction temperatures can be varied within a relatively wide range. In general, the process is carried out at temperatures from 80° C. to 200° C., preferably at temperatures from 120° C. to 150° C., particularly preferably at temperatures from 130° C. to 140° C.

The process b) according to the invention is generally carried out under atmospheric pressure. However, it is also possible to operate under elevated pressure—generally up to 10 bar.

For carrying out the process b) according to the invention for preparing the compounds of the formula (II), in general from 2 to 10 mol, preferably from 4 to 6 mol, of carboxylic anhydride of the formula (VI) or carbonyl chloride of the formula (VII) are employed per mole of the salicylic acid derivative of the formula (V).

The process b) according to the invention is generally carried out as follows: the salicylic acid derivative of the formula (V) is mixed with the carboxylic anhydride of the formula (VI) or the carbonyl chloride of the formula (VII) and the catalyst and heated. If a carboxylic anhydride of the formula (VI) is used, it may be advantageous to remove the carboxylic acid formed during the reaction via a distillation column. After the reaction has ended, the mixture is worked up in a customary manner. For example, the more volatile components are distilled off from the reaction mixture under slightly reduced pressure and the product is then distilled under strongly reduced pressure.

In a particularly preferred process variant, the benzofuranyl alkanoate of the formula (II) is not isolated but, after the volatile components from process b) have been distilled off, admixed directly with a diluent and an acid and then heated as described under process a). The further practice of the reaction and work-up are carried out as under process a). In this variant, it is particularly advantageous that it is not necessary to purify the benzofuranyl alkanoate of the formula (II).

The benzofuranone oximes of the formula (I) can be used as intermediates for preparing fungicides (compare, for example, EP-A 846 691).

The examples below serve to illustrate the invention. However, the invention is not limited to the examples.

PREPARATION EXAMPLES

Example 1

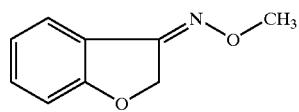

17.6 g (0.1 mol) of 3-acetoxy-benzofuran are dissolved in 100 ml of dimethoxyethane, and 6 ml of 20% strength hydrochloric acid are added. With stirring, the mixture is heated at 65° C. for two hours and then allowed to cool to about 30–35° C., and 33.4 g (0.12 mol) of a 30% strength aqueous solution of O-methylhydroxylamine hydrochloride are added. 12 g of sodium acetate are then added, and the mixture is heated at 40–45° C. for 4 hours. The solvent is distilled off under reduced pressure and the aqueous phase is diluted slightly and extracted three times with methylene chloride. This gives 14.2 g of —O-methyl benzofuran oxime which slowly begins to crystallize on standing.

M.p.: 38° C., log P 2.38

Yield: 87.0% of theory.

Example 2

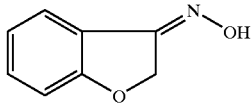

35.2 g (0.2 mol) of 3-acetoxy-benzofuran are dissolved in 180 ml of methanol, 9 ml of water and 4.9 g of 20% strength hydrochloric acid are added and the mixture is heated at the boil for 2 hours. The mixture is cooled to 35° C. and 23.9 g (0.284 mol) of sodium acetate and then 15.4 g (0.22 mol) of hydroxylammonium chloride are added. With stirring, the mixture is heated at 45° C. for 4.5 hours and then cooled, and the methanol is distilled off. The residue is admixed with 220 ml of water and the solid is filtered off. The product is washed with water and then with toluene and dried in a vacuum drying cabinet. This gives 28.2 g of slightly coloured crystals of a purity of 97%, which corresponds to a yield of 91.7% of theory.

M.p.: 157–159° C., log P 1.44

Example 3

Process (b)

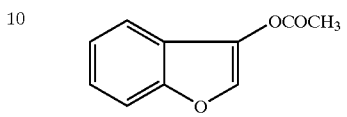

58.9 g (0.3 mol) of 2-carboxy-phenoxyacetic acid, 153 g (1.5 mol) of acetic anhydride and 1.2 g (0.015 mol) of pyridine are combined and heated to the boil. After 24 hours, acetic acid and excess acetic anhydride are distilled off and the last volatile components are removed at 35° C./5 mbar.

This gives 52.8 g of an oil which can be used directly for the next step. Purity: 97%, yield: 96.9% of theory.

Purification by distillation is not necessary, but possible: b.p.=85° C./0.05 mbar.

Analogously to Example 3, it is possible to prepare the following compounds:

TABLE 1

| Example | Formula | Yield | log P | m.p. |
|---|---|---|---|---|
| 4 | 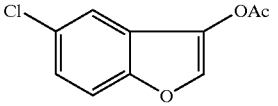 | | | |
| 5 | 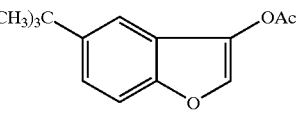 | 82.4% | 4.17 | Oil |
| 6 | 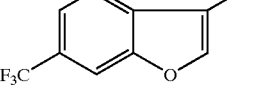 | 95.4% | 3.38 | 27° C. |
| 7 | 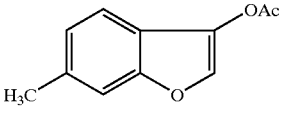 | 90.1% | 3.09 | 32–36° C. |
| 8 | 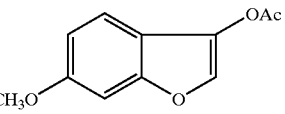 | 36% | 2.65 | Oil |

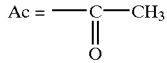

Analogously to Example 2, it is possible to prepare the following compounds:

| Example | Formula | Yield | log P | m.p. |
|---|---|---|---|---|
| 9 | 5-Cl-benzofuran-3(2H)-one oxime | | | |
| 10 | 5-t-(CH₃)₃C-benzofuran-3(2H)-one oxime | | | |
| 11 | 6-F₃C-benzofuran-3(2H)-one oxime | 84% | 2.38 | 150° C. (decomp.) |
| 12 | 6-H₃C-benzofuran-3(2H)-one oxime | 89% | 1.79 | 138° C. (decomp.) |
| 13 | 6-H₃CO-benzofuran-3(2H)-one oxime | 79% | 1.52 | 122–124° C. (decomp.) |

What is claimed is:

1. A process for preparing a compound of the Formula (I),

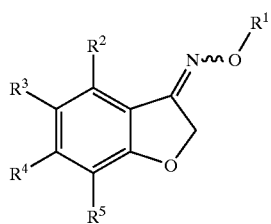

(I)

wherein
$R^1$ represents hydrogen or alkyl and
$R^2$, $R^3$, $R^4$ and $R^5$ are identical or different and independently of one another each represents hydrogen, alkyl, alkoxy, halogenoalkyl or halogen, comprising the steps of:
a) hydrolyzing a compound of the Formula (II),

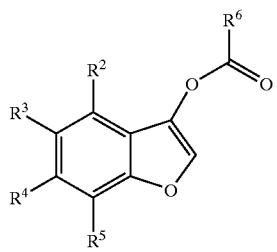

(II)

wherein
$R^2$, $R^3$, $R^4$ and $R^5$ are each as defined above
$R^6$ represents alkyl
using an acid, optionally in the presence of a diluent, resulting in the formation of a benzofuranone of the Formula (III),

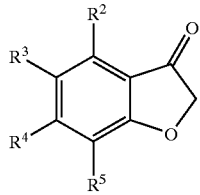

(III)

wherein
$R^2$, $R^3$, $R^4$ and $R^5$ are each as defined above, and
b) reacting said benzofuranone of the Formula (III) without work-up with a member selected from the group consisting of a hydroxylamine derivative of the Formula (IV),

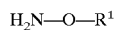 H₂N—O—R¹ (IV)

wherein
$R^1$ is as defined above, and an acid addition complex thereof, optionally in the presence of a diluent and optionally in the presence of a buffer medium, whereupon said compound of said Formula (I) is formed.

2. A process according to claim 1, wherein the step (b) of the reaction is carried out at a pH from 3 to 7 in acetic acid/sodium acetate as buffer mixture.

3. A process according to claim 1 wherein in said step (b), said benzofuranone is reacted with said hydroxylamine derivative or its acid addition complex.

4. A process according to claim 1, wherein a step selected from the group consisting of said step (a), said step (b) and combinations thereof occur in the presence of a solvent, and wherein the solvent is methanol.

5. A process for preparing a compound of the Formula (II),

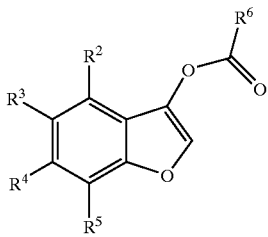

wherein $R^2$, $R^3$, $R^4$ and $R^5$ are identical or different and independently of one another each represents hydrogen, alkyl, alkoxy, halogenoalkoxy or halogen, and $R^6$ represents alkyl, comprising the step of:

reacting a compound of the Formula (V),

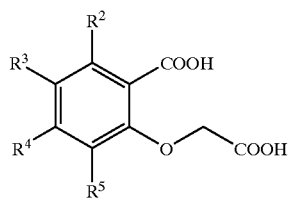

wherein $R^2$, $R^3$, $R^4$, $R^5$ are each as defined in this claim 5 above, with a member selected from the group consisting of an aliphatic acid anhydride of the Formula (VI)

wherein $R^6$ is as defined above in this claim 5 and an aliphatic acyl chloride of the Formula (VII),

wherein $R^6$ is as defined above in this claim 5, in the presence of a catalyst, whereupon the compound of the Formula (II) is formed.

6. A process according to claim 5, wherein the catalyst is a pyridine derivative.

7. A process according to claim 5, wherein said reacting step is carried out using acetic anhydride as said compound of the Formula (VI).

8. A process according to claim 5, wherein said reacting step is carried out in a temperature range from 120° C. to 150° C.

* * * * *